United States Patent [19]

Bohn et al.

[11] Patent Number: 4,746,731

[45] Date of Patent: May 24, 1988

[54] ISOLATED TISSUE PROTEIN PP$_{18}$

[75] Inventors: Hans Bohn, Marburg; Wilhelm Winckler, Wenkbach, both of Fed. Rep. of Germany

[73] Assignee: Behringwerke Aktiengesellschaft, Marburg/Lahn, Fed. Rep. of Germany

[21] Appl. No.: 735,060

[22] Filed: May 17, 1985

[30] Foreign Application Priority Data

May 21, 1984 [DE] Fed. Rep. of Germany ....... 3418888

[51] Int. Cl.$^4$ ....................... C07K 3/00; C07K 15/00; C07K 15/06; C07K 15/14
[52] U.S. Cl. ..................... 530/394; 436/543; 436/811; 424/85; 530/350; 530/395; 530/414; 530/415
[58] Field of Search .................. 424/105, 85; 530/350, 530/386, 394, 851, 395, 414, 415; 436/501, 518, 536, 543, 811

[56] References Cited

U.S. PATENT DOCUMENTS

| | | | |
|---|---|---|---|
| 3,979,507 | 9/1976 | Baker | 436/536 |
| 4,254,021 | 3/1981 | Bohn et al. | 530/394 |
| 4,297,274 | 10/1981 | Bohn et al. | |
| 4,301,064 | 11/1981 | Bohn | 424/105 |
| 4,302,385 | 11/1981 | Bohn et al. | 436/543 |
| 4,368,148 | 1/1983 | Bohn | 424/105 |
| 4,468,345 | 8/1984 | Bohn et al. | 436/543 |

FOREIGN PATENT DOCUMENTS

| | | | |
|---|---|---|---|
| 2842467 | 4/1980 | Fed. Rep. of Germany | 436/543 |
| 3013724 | 10/1981 | Fed. Rep. of Germany | 530/394 |
| 3230996 | 2/1984 | Fed. Rep. of Germany | 424/105 |

*Primary Examiner*—David M. Naff
*Assistant Examiner*—Florina B. Hoffer
*Attorney, Agent, or Firm*—Finnegan, Henderson, Farabow, Garrett & Dunner

[57] ABSTRACT

A protein PP$_{18}$ is isolated having the following characteristics:
(a) an electrophoretic mobility in the region of that of $\beta_1$-globulins;
(b) an isoelectric point between 5.6 and 6.2;
(c) a sedimentation coefficient $s_{20,w}$ of 5.0±0.2 S;
(d) a molecular weight determined in an ultracentrifuge of 82,300±5,600;
(e) a carbohydrate fraction of 2.3±1.3 g/100 g (mannose 0.15±0.1, xylose 0.5±0.5, galactose 0.5±0.2, glucose 0.2±0.1, N-acetylglucosamine 0.7±0.2, and N-acetylneuraminic acid 0.25±0.2, each g/100 g).

Also described is the amino acid composition of the protein and a process for its isolation. Antiserum is prepared and used in an immunoassay to detect the protein.

1 Claim, 1 Drawing Sheet

ISOLATED TISSUE PROTEIN PP$_{18}$

The invention relates to a tissue protein, called PP$_{18}$, and to a process for obtaining it. PP$_{18}$ can be used to prepare antisera which can be employed for the detection and determination of PP$_{18}$ in tissue and body fluids in order in diagnose diseases of particular organs, as a "marker" for monitoring the course of an illness or for monitoring a treatment.

Proteins are of course known in the state of the art, including tissue proteins, but none having the properties indicated below for PP$_{18}$.

The invention relates to the protein PP$_{18}$ which has the following characteristics:
- (a) an electrophoretic mobility in the region of that of $\beta_1$-globulins;
- (b) an isoelectric point between 5.6 and 6.2;
- (c) a sedimentation coefficient $s_{20,w}$ of $5.0 \pm 0.2$ S;
- (d) a molecular weight determined in an ultracentrifuge of $82,300 \pm 5,600$; and
- (e) a carbohydrate fraction of $2.3 \pm 1.3$ g/100 g (mannose $0.15 \pm 0.1$, xylose $0.5 \pm 0.5$, galactose 0.5–0.2, glucose $0.2 \pm 0.1$, N-acetylglucosamine $0.7 \pm 0.2$, and N-acetylneuraminic acid $0.25 \pm 0.2$, each g/100 g).

The amino acid composition of PP$_{18}$ is shown in the Table below:

| Amino acid | Residues per 100 residues | Coefficient of variation |
|---|---|---|
| Lysine | 5.26 | 0.13 |
| Histidine | 2.20 | 7.71 |
| Arginine | 5.53 | 1.41 |
| Aspartic acid | 9.26 | 4.20 |
| Threonine | 3.60 | 4.32 |
| Serine | 5.21 | 2.58 |
| Glutamic acid | 10.37 | 0.82 |
| Proline | 8.13 | 1.48 |
| Glycine | 7.18 | 0.30 |
| Alanine | 4.97 | 1.00 |
| Cystine ½ | 1.78 | 0.79 |
| Valine | 9.05 | 1.09 |
| Methionine | 3.00 | 1.65 |
| Isoleucine | 3.33 | 2.55 |
| Leucine | 11.81 | 0.66 |
| Tyrosine | 2.37 | 4.77 |
| Phenylalanine | 4.21 | 1.51 |
| Tryptophan | 2.70 | 1.84 |

The following may be detailed to explain the characterizing features of the tissue protein:

The electrophoretic mobility was determined in the micro modification on cellulose acetate films (supplied by Sartorius) using sodium diethylbarbiturate buffer, pH 8.6, and a microzone R 200 apparatus from Beckman Instruments.

The isoelectric point was measured using a column (440 ml) supplied by LKB, Stockholm. The Ampholin ® mixture had a pH range from 5.0 to 8.0.

The sedimentation coefficient was determined in an analytical ultracentrifuge supplied by Beckman (Spinco Apparatus, model E) at 60,000 rpm, in double-sector cells using the UV scanner technique at 280 nm. The solvent used was water. The protein concentration was 2 g/l.

The sedimentation equilibrium method was used to determine the molecular weight in the ultracentrifuge. The concentration of the protein was adjusted to about 1.0 O.D. (optical density) for this purpose. The solvent used was a 0.05 mol/l phosphate buffer (pH 6.8) which contained 0.2 mol/l NaCl. The determination was carried out at 9,000 rpm. Recording was carried out at 280 nm using a photoelectric scanner.

The carbohydrates were determined as follows:

After hydrolysis of the glycosidic bonds, the liberated neutral sugars were separated as borate complexes on an anion exchanger column (Y. C. Lee et al., Anal. Biochem. 27 (1969), 567), stained in the eluate by admixture of Cu(I) bicinchoninate reagent (K. Mopper and M. Gindler, Anal. Biochem. 56 (1973), 440) and determined quantitatively using rhamnose as the internal standard. The amino sugars were detected and determined by their reaction with ninhydrin. The neuraminic acid content was measured by the method of Warren (Methods in Enzymology, Vol. VI (1963), 463–465).

The amino acid analysis was carried out by the method of S. Moore, D. H. Spackman, W. H. Stein, Anal. Chem. 30 (1958), 1185, using a Multichrom B liquid chromatograph supplied by Beckman. Cystine was determined as cysteic acid following oxidation of the protein with performic acid (S. Moore et al., Anal. Chem. 30 (1958), 1185) and subsequent chromatography (S. Moore, J. Biol. Chem. 238 (1963), 235). The tryptophan content was measured by direct photometric determination by the method of H. Edelhoch, Biochemistry 6 (1967), 1948.

On investigation of extracts from various human organs using immunochemical methods, PP$_{18}$ was detected in relatively low concentrations in placenta, adrenal and stomach. Extracts of other human organs, such as heart, lung, liver, kidney, colon, rectum, jejunum and uterus either do not contain this protein or contain only traces of it. Proteins which are immunochemically identical or closely related to PP$_{18}$ have also been detected in extracts or rhesus monkey placentae.

Accordingly, human, as well as animal, organs in which PP$_{18}$ occurs can be used for the isolation of this protein. Mature human placentae are particularly suitable for this purpose, since they are produced in large quantities and they contain the protein in a sufficiently high concentration.

A mature human placenta contains on average about 2 mg of PP$_{18}$.

PP$_{18}$ has the following properties which can be used in a process for its isolation, by employing measures appropriate for these properties:
- (1) it is precipitated from aqueous solutions with ammonium sulfate at a pH of 5–8 and 30–50% saturation;
- (2) It is substantially precipitated with water-soluble acridine bases, for example 2-ethoxy-6,9-diaminoacridine lactate, at a pH of 7–9 and a concentration of the base of 4 to 8 g/l. It is not precipitated at a pH of 6.0 and a base concentration of 4 g/l;
- (3) it remains substantially in the supernatant on addition of ethanol to a solution in a physiological saline solution, or one of similar dilution, at pH 7, up to a concentration of 200 ml of alcohol per l of solution;
- (4) on fractionation by electrophoresis, at a pH of 7–9, it is found in the region of the $\beta_{1\text{-}globulins}$;
- (5) on isoelectric focusing, it appears in the pH range 5.6 to 6.2;
- (6) on gel filtration using Sephadex ®, it behaves like proteins having molecular weights of 60,000 to 100,000;

(7) it can be bound to weakly basic ion exchangers, for example DEAE-cellulose or DEAE-Sephadex, at a conductivity of about 0-2 mS and a pH of about 7 to 9, and can be eluted with more concentrated salt solutions (10-50 g/l NaCl solutions);

(8) it can be enriched in and isolated from an aqueous solution by immunoadsorption.

Accordingly, the invention also relates to a process for obtaining or enriching $PP_{18}$, which comprises subjecting an extract obtained, using dilute salt or buffer solutions, from organs which contain this protein to one or more of the following measures:

(a) precipitation of the protein $PP_{18}$ with ammonium sulfate in the pH range 5 to 8 and at 30-50% saturation;

(b) separation out of concomitant proteins using a water-soluble acridine base at a pH of 6 and a concentration of the base of 4 g/l or less, or precipitation of the protein $PP_{18}$ using a water-soluble acridine base at a pH between 7 and 9 and a concentration of the base of 4 to 8 g/l;

(c) separation out of part of the concomitant proteins by addition of ethanol, at pH 7, to a final concentration of 200 ml/l alcohol;

(d) preparative zone electrophoresis, where the protein fraction in the region of the $\beta_1$-globulins is obtained;

(e) gel filtration or ultrafiltration, where proteins in the molecular weight range 60,000 to 100,000 are obtained;

(f) adsorption on a weakly basic ion exchanger and elution of the protein $PP_{18}$;

(g) enrichment by immunoadsorption.

Apart from ammonium sulfate, it is also possible to use for the precipitation of $PP_{18}$ other neutral salts customarily used in preparative biochemistry. Apart from an acridine base, it is also possible to use within the scope of the process according to the invention a water-soluble derivative of a quinoline base, such as are known for protein fractionations. As appropriate for its electrophoretic behavior, its charge and its molecular weight, it is also possible to apply to the isolation of the protein other measures which are suitable for separating a protein having the indicated properties from other proteins.

It is possible to use for this purpose the various methods of preparative electrophoresis, isoelectric focusing, gel filtration or ultrafiltration, as well as the property of $PP_{18}$ of being able to be bound to weakly basic ion exchangers and eluted again from them.

In particular, it is possible to isolate $PP_{18}$ by an appropriate combination of the measures mentioned, which bring about enrichment of $PP_{18}$ or separation of this protein from other proteins.

The Example describes the isolation of $PP_{18}$ by use of the method of immunoadsorption. It would be possible the use the aqueous extract from human placentae directly for the immunoadsorption. Since the concentration of $PP_{18}$ in the extract is relatively low, it is advantageous initially to carry out a specific enrichment of the protein $PP_{18}$ by preliminary fractionation of the extract.

However, the steps for the enrichment indicated in the Example are not obligatory and need not by any means be carried out in the sequence described there.

It would also be possible to replace the immunoadsorption step by the use of other separation methods, for example by preparative electrophoresis and isoelectric focusing.

Apart from the parameters indicated, it is also possible to use immunochemical methods for the detection and determination of $PP_{18}$, for example in a fraction from a separation operation, since $PP_{18}$ has antigenic properties.

An antiserum which can be used for this purpose can be obtained as follows:

On fractionation of a placental extract with 2-ethoxy-6,9-diaminoacridine lactate and ammonium sulfate by the method of Bohn, H., (Arch. Gynäkol. (1971) 210, 440), most of the $PP_{18}$ goes into placental fraction III. If this fraction is further fractionated by gel filtration on Sephadex G-150, then $PP_{18}$ appears in the region of the proteins with molecular weights between 60,000 and 100,000. A polyvalent antiserum which contains, inter alia, antibodies to $PP_{18}$ is obtained by immunization of rabbits with this fraction. This antiserum can be made substantially specific to the antigen $PP_{18}$ by absorption with normal human serum and with placental fractions which do not contain $PP_{18}$.

This antiserum can be used, on the one hand, for the immunological detection of $PP_{18}$ and, on the other hand, for the preparation of an immunoadsorbent which can be employed for the enrichment and isolation of $PP_{18}$.

Monospecific antisera can be prepared, by immunization of animals by known methods, using the purified $PP_{18}$ obtained in accordance with the Example of the present application.

BRIEF DESCRIPTION OF THE DRAWINGS

FIG. 1a shows the immunological reaction of $PP_{18}$ with a specific antiserum from rabbits, after fractionation in an electric field in agar-containing gel.

For comparison with this,

FIG. 1b shows the fractionation of the proteins in the serum, visualized by their immune reaction with a rabbit antiserum to human serum (HS).

It is also possible to employ for the immunological detection of $PP_{18}$ the Ouchterlony gel diffusion technique (Schultze and Heremans, Molecular Biology of Human Proteins, vol. 1, page 134) or, if necessary, more sensitive methods, such as radioimmunoassays or enzyme immunoassays.

The detection and determination of $PP_{18}$ have diagnostic significance. $PP_{18}$ is a tissue protein which occurs in relatively high concentration only in particular organs. When there is a disease of these organs, as a consequence of increased cell death there can be an increase above normal in the concentration of the tissue protein $PP_{18}$ in the serum or in other body fluids of the patients. The detection and determination of $PP_{18}$ in body fluids can thus be used for the diagnosis of diseases of these organs or as a marker for monitoring the course of the illness and for monitoring the treatment.

Thus, $PP_{18}$ can be used to prepare antisera which can be employed to detect and to determine $PP_{18}$ and to design immunochemical methods.

The invention is illustrated by the Example which follows:

EXAMPLE (A) Extraction of the placentae and fractionation of the extract using an acridine base and ammonium sulfate 1,000 kg of deep-frozen human placentae were comminuted in a cutter-mixer and extracted with 1,000 l of a 4 g/l sodium chloride solution. After removal of the tissue residue by centrifugation, the extract was then adjusted to pH 6.0 with 200 ml/l acetic acid solution and, with stirring, 200 l of a 30 g/l solution of 2-ethoxy-6,9-diaminoacridine lactate (Hoechst AG) were added. The precipitate was removed by centrifugation and discarded. 10 g/l Betonit A (supplied by Erbslöh and Co., Geisenheim/Rhein) were added to the supernatant, the pH was adjusted to 7.0 by addition of 2N NaOH, and the mixture was filtered. 300 g/l ammonium sulfate was slowly added, with stirring, to the filtrate; this resulted in the placentral protein $PP_{18}$ precipitating out together with other proteins. The precipitate was filtered off. About 12 g of a moist paste were obtained, and this is denoted fraction A below.

(B) Fractionation with ethanol 500 g of fraction A were dissolved in 400 ml of water and the solution was dialyzed against physiological saline solution at 4° C. After the dialysis, the conductivity of the solution was adjusted to 15 mS by addition of a 50 g/l NaCl solution. The solution was then cooled to 0° C. and, with stirring, ethanol containing 960 g/l was slowly added to a final concentration of the alcohol of 200 g/l. The precipitate was removed by centrifugation. The supernatant was dialyzed first against water and then against a 0.1 mol/l tris HCl buffer (pH 8.0), which contained 1 mol/l NaCl and 1 g/l $NaN_3$ (buffer solution II). The proteins were then precipitated out by addition of 380 g/l solid ammonium sulfate. The precipitate was dissolved in water and dialyzed against buffer solution II. About 1,000 ml of a solution (fraction B), which contained on average 160 mg of $PP_{18}$, were obtained.

(C) Enrichment of $PP_{18}$ by immunoadsorbtion

1. Preparation of the immunoadsorbent 300 ml of a rabbit anti-$PP_{18}$ serum were dialyzed against 0.02 mol/l phosphate buffer (pH 7.0), and chromatographed on DEAE-cellulose to remove the immunoglobulins. This entails the immunoglobulins migrating unhindered through the DEAE-cellulose, while the other serum proteins are mostly adsorbed onto the DEAE-cellulose. The immunoglobulin fraction (2.62 g of protein) which ran through was then reacted with 262 g of specially purified agarose in the form of beads (Sepharose ® 4 B supplied by Pharmacia, Uppsala, Sweden) which had been activated with 32.7 g of cyanogen bromide, and thus was covalently bonded to a carrier. A suitable process is described by, for example, Axen et al., Nature 124, 1302 (1967).

It was possible to isolate the protein $PP_{18}$ from its solution, in particular from placental fractions enriched in $PP_{18}$, using an immunoadsorbent prepared in this manner.

2. Immunoadsorption procedure

The immunoadsorbent was suspended in buffer solution II (0.1 mol/l tris HCl buffer, pH 8.0, containing 1.0 mol/l NaCl and 1 g/l $NaN_3$), and a chromatography column (5.0×15 cm) was packed with it and washed with buffer solution II. Then half the amount of fraction B was applied to the column, the $PP_{18}$ being bound by immunoadsorption. The column was thoroughly washed with buffer II. The adsorbed protein was then eluted from the column using about 600 ml of 3 mol/l potassium thiocyanate solution. The eluates containing $PP_{18}$ were dialyzed against buffer solution II and concentrated to about 10 ml in an ultrafilter. Yield per adsorption about 6 mg of $PP_{18}$.

Immediately after the elution of $PP_{18}$, the adsorbent in the column was neutralized again, and thoroughly washed, with buffer solution II. It was then reused for the binding of $PP_{18}$ by immunoadsorption.

(D) Final purification of $PP_{18}$

The protein obtained by immunoadsorption was frequently still contaminated by non-specifically bound serum proteins and other placental proteins. The main amount of the concomitant proteins were removed by gel filtration on Ultrogel ® AcA 34 followed by ion exchange chromatography on DEAE-Sephadex. The proteins adsorbed onto DEAE-Sephadex were eluted using a linear salt gradient from 0 to 20 g/l sodium chloride in 0.01 mol/l tris HCl buffer (pH 7.0). $PP_{18}$ was detected in the fractions using immunochemical methods. The fractions which contained the main amount of $PP_{18}$ were combined and concentrated in an ultrafilter. The remaining concomitant proteins were then removed by inverse or negative immunoadsorption, that is to say using carrier-bound antibodies to the proteins still present as contaminants. For the preparation of antibodies to these concomitant proteins, a portion of the crude $PP_{18}$ fraction was dialyzed against a 0.5M glycine HCl buffer (pH 2.5) for 12 hours and then neutralized again. Under these conditions, $PP_{18}$ undergoes denaturation and loses its immunochemical reactivity; in contrast, the contaminants are stable and remain as antigens. When animals are immunized with this, then antibodies to those proteins are obtained and, while after binding to a carrier, can be used for the removal by immunoadsorption of the unknown placental proteins from the crude $PP_{18}$ fraction.

We claim:

1. An isolated, concentrated tissue protein, $PP_{18}$, obtained by fractionating an extract of human organs, said tissue protein having:
    (a) an electrophoretic mobility in the region of that of $\beta_1$-globulins;
    (b) an isoelectric point between 5.6 and 6.2;
    (c) a sedimentation coefficient $s_{20,w}$ of $5.0\pm0.2$ S;
    (d) a molecular weight determined in an ultracentrifuge of $82,300\pm5,600$; and
    (e) a carbohydrate fraction of $2.3\pm1.3$ g/100 g (mannose $0.15\pm0.1$, xylose $0.5\pm0.5$, galactose $0.5\pm0.2$, glucose $0.2\pm0.1$, N-acetylgucosamine $0.7\pm0.2$, and N-acetylneuraminic acid $0.25\pm0.2$, each g/100 g).

* * * * *